United States Patent [19]

Sumi Horvath et al.

[11] Patent Number: 5,723,487

[45] Date of Patent: Mar. 3, 1998

[54] PREPARATION OF A PRODUCT FOR TREATMENT OF COLAGEN-RELATED DISORDERS

[76] Inventors: Antonio Sumi Horvath, deceased. late of Santiago; by Judith Tobar Goycolea, legal representative. M. Luisa Santander 0191 Providencia Stgo, Santiago; by Antonio Sumi Horvath, legal representative. 306 Y Nar 90 Dep 53, Vina del Mar; by Dora Kiss Horvath, legal representative. Pasale La Villa 8241, Santiago, all of Chile

[21] Appl. No.: 387,068

[22] Filed: Feb. 13, 1995

[51] Int. Cl.[6] ................................................. A61K 31/335

[52] U.S. Cl. .............................................. 514/449; 549/300

[58] Field of Search ............................... 549/300; 514/449

[56] References Cited

PUBLICATIONS

Yves Lacassie, Poster Presentation at (4 sheets) VII International Congress of Human Genetics, Berlin 1986.

*Primary Examiner*—Amelia Owens
*Attorney, Agent, or Firm*—Michael L. Murray

[57] ABSTRACT

This invention refers to a process for creating a product useful in the treatment of disorders related to collagen production and function.

4 Claims, No Drawings

PREPARATION OF A PRODUCT FOR TREATMENT OF COLAGEN-RELATED DISORDERS

BACKGROUND OF THE INVENTION

In spite of extensive advances in the understanding of the biochemistry, physiology, and genetics of collagen production and function within the body, there is no therapy capable of improving many collagen-related disorders. These diseases include osteogenesis imperfecta (O.I.), arthritis, degenerative joint disease, discospondylitis, hip dysplasia, scleroderma, rosacea, and epidermolysis bullosa, among others; see Tilstra and Byers, 1994, *Annu. Rev. Med.* 45:149–153 (incorporated herein by reference).

O.I. is a highly heterogeneous group of hereditary disorders of the connective tissue, fundamentally characterized by bone fragility with multiple fractures. In many cases the increased brittleness of the bones is associated with other signs such as blue sclerae, dentinogenesis imperfecta, impaired hearing, hyperlaxity of the joints and easy bruising of the skin. There exists clinical, genetic and biochemical heterogeneity in forms of this disease. The disease is reviewed by Byers and Steiner, 1992, Annual Review of Medicine; 43: 269–82 (incorporated herein by reference).

Certain types of cancer are also collagen-related disorders, in particular, those tumors that invade adjacent tissues by their collagenase activity. Highly aggressive human tumors such as carcinomas, melanomas, hepatomas, fibrosarcomas, and reticulum cell sarcoma have metastatic potential that positively correlates with collagenase activity. See Liotta et al. 1991, in *Molecular Foundations of Oncology*, ed. S. Broder, Williams & Wilkins, Baltimore, pp. 57–81 (incorporated herein by reference).

In summary, currently there is no effective treatment for a large variety of collagen disorders and some related cancers.

SUMMARY OF THE INVENTION

It has been found that a synthetic non-toxic, non-teratogenic, delta (beta-cetonic) lactone called JH-11 has beneficial therapeutic effect on disorders characterized by defects in collagen biosynthesis, physiology or genetics; these diseases include rheumatoid arthritis, osteoarthritis, degenerative joint disease, discospondylitis, hip dysplasia, scleroderma, epidermolysis bullosa, and osteogenesis imperfecta (O.I.), among others. For a description of collagen-related disorders, see Varga et al., 1994, Clin. Dermatol. 12:387–396 (incorporated herein by reference).

For the purposes of this invention "synthetic JH-11" is the product of the following process:

a) provide a solution of an ascorbate in ethanol;
b) provide a solution of sodium hydroxide dissolved in water;
c) mix the ascorbate solution with the sodium hydroxide solution so that the molar ratio of sodium hydroxide to ascorbate is 0.7:1 and an alkaline pH is maintained;
d) mix chloroform with the solution of step c in quantity sufficient to produce a crystalline substance;
e) collect the crystalline substance, the substance having a decomposition temperature of approximately 170° C.;
f) maintain the temperature of all steps below approximately 35° C.

For the purposes of this invention, a method of treating collagen related disorders comprises the following process:

a) provide a solution of an ascorbate in ethanol;
b) provide a solution of sodium hydroxide dissolved in water;
c) mix the ascorbate solution with the sodium hydroxide solution so that the molar ratio of sodium hydroxide to ascorbate is 0.7:1 and an alkaline pH is maintained;
d) mix chloroform with the solution of step c in quantity sufficient to produce a crystalline substance;
e) collect the crystalline substance, the substance having a decomposition temperature of approximately 170° C.;
f) maintain the temperature of all steps below approximately 35° C.;
g) administer to a mammal in need thereof, especially a feline mammal or a human, a therapeutically effective amount of the crystalline substance.

DETAILED DESCRIPTION OF THE INVENTION

The present inventor has tested JH-11 for therapeutic effect in animals affected by O.I.-like disease and on human patients with several types of O.I.; both the animal tests and the human tests demonstrated a beneficial therapeutic effect on O.I. associated manifestations.

Treatment of O.I.-like syndrome in felines with JH-11 is described by Horvath et al., 1986, Avances en Ciencias Veterinarias; 1:49–51 (incorporated herein by reference). The feline O.I.-like syndrome responds favorably to treatment with JH-11. A male tiger, weighing 50 kg at 8 months from birth, staying prostrate due to the presence of fractures on both posterior extremities was treated for 10 months with 100 mg of JH-11 per day. The JH-11 used for treatment was derived from the saccharide part of calagualine and it was provided in a gelatin capsule with lactose as a carrier. After 3 months of daily treatment with JH-11, X-ray radiographs of the tiger's femurs and tibias showed the fractures consolidating and calcifying. The tiger's weight increased to 80 kg, and he recovered the activity and aggressiveness characteristic of this species. The condition of the teeth and nails of the tiger also improved. The treatment was finished after 10 months.

JH-11 therapy was also tested in a group of patients with O.I. The diagnosis for each patient was clinically and radiologically established and classified into subgroups according to Sillence et al., 1979, J. Med. Genet. 16:101–116 (incorporated herein by reference). The patients were given 100 mg of JH-11 in a gelatine capsule orally before eating at lunch time under parental supervision. Table 1 shows the main clinical features, the Sillence O.I. type, pre- and post-treatment frequency of fractures, age at diagnosis and dates and duration of treatment for a group of 14 patients. Table 2 shows the Sillence O.I. type, pre- and post-treatment frequency of fractures, age at diagnosis and dates and duration of treatment for a group of 24 patients; the patients from Table 1 are repeated as patients 1 through 14 in Table 2. Table 3 shows the responses to a questionnaire administered to the parents and the referring physicians at the end of treatment. It is evident from these data that the treatment provides beneficial effects as measured by the objective decrease in fracture frequency and by the subjective reaction of the parents and referring physicians.

No adverse affects have been detected in the group of patients. Some patients have completed up to 10 years of treatment with no problems. Urine and serum tests have been normal, except that an increased level of ascorbic acid or ascorbic-like substance in urine has been observed.

JH-11 also has beneficial effects on certain types of cancer, in particular those that invade adjacent tissues by their collagenase activity. Canine mammary malignant tumors were used as a model for testing the effect of JH-11 on malignant tumors possessing collagenase activity. These tumors are both spontaneous and multiple. Approximately half of the tumors were removed. After one month of treatment, using 60 to 100 mg per day of JH-11, the remaining tumors showed involution and hardness. X-ray radiographic examination and hematoxilin-eosine and MBTH specific staining for collagen showed proliferation of fibrous collagen and its calcification around the remaining tumors. MBTH staining is described by Horvath et. al, 1981, Acta anat; 111:314–319 (incorporated herein by reference) and by Horvath et al. 1983, Acta anat; 115:238–243 (incorporated herein by reference). Radio-labelled amino acid incorporation into the collagen during the treatment of tumor bearing dogs revealed that by the 10th day there was an in situ induction of collagen synthesis.

PREPARATION OF JH-11

JH-11 has been synthesized from the carbohydrate moiety of calagualine as described by Horvath et al, 1986; Avances en Ciencias Veterinarias; 1:49–51. Calagualine is a saponine, formed by a ketosteroid and a deoxyhexose, see Horvath et al, Nature, 1967; 214: 1256–1258 (incorporated herein by reference).

PREPARATION OF JH-11, PROSPECTIVE EXAMPLE

JH-11 is also synthesized by treating a salt of ascorbic acid with a polar organic solvent, an alkyl halide solvent and an aqueous solution of an alkali metal compound. The molar ratio of the alkali metal to the ascorbate is approximately 0.7 to 1.0. The mixture is reacted at room temperature (approximately 15° C. to 25° C., not over 35° C.). For the polar organic solvent, one skilled in the art would select alcohols such as methanol, ethanol and propanol, and polar solvents such as acetonitrile, dimethyl sulfoxide, N,N-dimethyl formaldehyde. For the alkali metal, one skilled in the art would select lithium hydroxide, potassium hydroxide, or sodium hydroxide, etc. For the alkyl halide solvent, one skilled in the art would select chloroform, methylene dichloride, carbon tetrachloride, etc. Any ascorbate salt may be used so long as it advances the reaction. The wording "ascorbate" as referred to in the invention means an L-ascorbic acid in the form of salts such as alkaline metals and alkaline-earth metals and mixtures thereof, as long as the selection does not cause any inconvenience. The reaction product is a white crystalline powder freely soluble in water, it is not hygroscopic and it decomposes at 170° C. This non-hygroscopic white crystalline powder, the object of this invention, is not a defined chemical substance, but a composition resulting from the methods of preparation and extraction.

WORKING EXAMPLE

Fifty grams of sodium ascorbate and 600 mls of methanol were placed in a 4 liter erlenmeyer flask (borosilicate glass). The mixture was stirred with a magnetic stirrer until dissolved, while the top of the flask was sealed with aluminum foil. Once dissolved (30 to 40 minutes) aluminum foil was removed and 40 mls of chloroform were added. Ninety milliliters of a 2 normal solution of sodium hydroxide was slowly poured into the erlenmeyer flask through a plastic funnel of 15 cms upper diameter from a 250 ml volumetric flask. The volumetric flask was kept sealed with a plastic cover when not in use. Stirring was continued until a fine opalescence appeared. Immediately 1 liter of chloroform was poured into the mixture and stirring was continued with no interruption until the bottom and the wall of the erlenmeyer flask was covered with crystalline material. The flask was removed from the magnetic stirrer and the magnet was removed with a retriever. The flask was sealed with aluminum foil and put to rest until the mixture of solvents was completely clear. The procedure has also been performed successfully with the use of mechanical agitation instead of stirring with a magnetic stirrer.

A filtration flask was prepared using a wide mouth 5 liter amber flask containing 1 liter of demineralized water. A plastic funnel of 30 centimeters (cms) upper diameter, 5 cms lower diameter, and a 15 cm stem, was lined with a folded #15 Ederal filter paper. The funnel was inserted into the filtration flask. The erlenmeyer flask was stirred vigorously to remove the adhered product, and the product and solvent were filtered using the filtration flask. The product was collected on the filter paper and dried with warm (not over 35° C.) dry air, and weighed. Yield was 30 to 35 grams of JH-11.

Substance and solvent was not in contact with metal throughout the procedure. Moreover, no vacuum was used, and humid air and water were excluded.

The product was a white crystalline powder freely soluble in water, it was not hygroscopic and it decomposed at 170° C. Ascorbic acid decomposes at 190° C. (Merck Index 11th ed., 855) (incorporated herein by reference) and sodium ascorbate at 218° C. (Merck Index 11th ed., 8525) (incorporated herein by reference).

It is well known to those skilled in the art that variations in the use of filter papers, vessels, and the like would not substantially alter the product.

What is claimed is:

1. A method of treating collagen related disorders comprising the following steps:
   a) providing a solution of an ascorbate in ethanol;
   b) providing a solution of sodium hydroxide dissolved in water;
   c) mixing the ascorbate solution with the sodium hydroxide solution so that the molar ratio of sodium hydroxide to ascorbate is 0.7:1 and an alkaline pH is maintained;
   d) mixing chloroform with the solution of step c in quantity sufficient to produce a crystalline substance;
   e) collecting the crystalline substance;
   f) determining a melting temperature of the crystalline substance;
   g) maintaining the temperature of all steps below approximately 35° C.;
   h) administering to a mammal in need thereof a therapeutically effective amount of the crystalline substance, if the melting temperature observed in step f is approximately 170° C.

2. The method of claim 1 wherein a therapeutically effective amount of the crystalline substance is approximately 100 mg.

3. The method of claim 1 wherein the mammal is chosen from the group consisting of feline animals and humans.

4. The method of claim 1 wherein the collagen related disorder is chosen from the group consisting of osteogenesis imperfecta and tumours that invade adjacent tissues by their collagenase activity.

* * * * *